United States Patent [19]

Buss et al.

[11] Patent Number: 4,721,695

[45] Date of Patent: * Jan. 26, 1988

[54] PLATINUM-BARIUM-ZEOLITE OF L FAMILY

[75] Inventors: Waldeen C. Buss, Kensington; Thomas R. Hughes, Orinda, both of Calif.

[73] Assignee: Chevron Research Company, San Francisco, Calif.

[*] Notice: The portion of the term of this patent subsequent to Jan. 26, 2005 has been disclaimed.

[21] Appl. No.: 889,984

[22] Filed: Jul. 24, 1986

Related U.S. Application Data

[60] Division of Ser. No. 392,907, Jun. 28, 1982, Pat. No. 4,645,588, which is a continuation-in-part of Ser. No. 344,570, Feb. 1, 1982, abandoned.

[51] Int. Cl.$^4$ ............................................. B01J 29/32
[52] U.S. Cl. ........................................ 502/66; 502/74
[58] Field of Search ...................... 502/66, 74; 208/138

[56] References Cited

U.S. PATENT DOCUMENTS

| 3,397,137 | 8/1968 | Pickert et al. | 208/138 |
| 3,783,123 | 1/1974 | Young | 208/111 |
| 4,104,320 | 8/1978 | Bernard et al. | 260/673.5 |
| 4,268,702 | 5/1981 | Duprez et al. | 208/138 |
| 4,443,326 | 4/1984 | Field | 208/138 |
| 4,478,706 | 10/1984 | Cohen | 208/138 |
| 4,517,306 | 5/1985 | Buss | 502/66 |
| 4,595,670 | 6/1986 | Tauster et al. | 502/66 |

FOREIGN PATENT DOCUMENTS

| 895280 | 3/1972 | Canada. |
| 981094 | 1/1965 | United Kingdom. |
| 1074129 | 6/1967 | United Kingdom. |
| 1161071 | 8/1969 | United Kingdom. |
| 1183000 | 3/1970 | United Kingdom. |
| 1497526 | 1/1978 | United Kingdom. |

OTHER PUBLICATIONS

J. R. Bernard, "Hydrocarbons Armatization on Platinum Alkaline Zeolites", Proceed. 5th Int'l Conf. on Zeolites, 686-695 (1980).

Primary Examiner—Carl F. Dees
Attorney, Agent, or Firm—S. R. La Paglia; T. G. DeJonghe; P. L. McGarrigle, Jr.

[57] ABSTRACT

A new catalyst is disclosed which is useful for dehydrocyclizing alkanes. This catalyst contains a zeolite of the L family, a Group VIII metal, and an alkaline earth metal.

5 Claims, No Drawings

PLATINUM-BARIUM-ZEOLITE OF L FAMILY

CROSS REFERENCE TO RELATED CASES

This is a division of application Ser. No. 392,907, filed June 28, 1982 now U.S. Pat. No. 4,645,588 which is a continuation-in-part of application Ser. No. 344,570, filed Feb. 1, 1982 and now abandoned.

BACKGROUND OF THE INVENTION

The invention relates to a new catalyst and a method using that catalyst in reforming hydrocarbons, more particularly hydrocarbons comprising paraffins containing at least 6 carbon atoms, to form the corresponding aromatic hydrocarbons.

Catalytic reforming is well known in the petroleum industry and refers to the treatment of naphtha fractions to improve the octane rating. The more important hydrocarbon reactions occurring during reforming operation include dehydrogenation of cyclohexanes to aromatics, dehydroisomerization of alkylcyclopentanes to aromatics, and dehydrocyclization of paraffins to aromatics. Hydrocracking reactions which produce high yields of light gaseous hydrocarbons, e.g., methane, ethane, propane and butane are to be particularly minimized during reforming as this decreases the yield of gasoline boiling products.

Dehydrocyclization is one of the main reactions in the reforming process. The conventional methods of performing these dehydrocyclization reactions are based on the use of catalysts comprising a noble metal on a carrier. Known catalysts of this kind are based on alumina carrying 0.2% to 0.8% by weight of platinum and preferably a second auxiliary metal.

The possibility of using carriers other than alumina has also been studied and it was proposed to use certain molecular sieves such as X and Y zeolites, which appeared suitable provided that the reactant and product molecules were sufficiently small to pass through the pores of the zeolite. However, catalysts based upon these molecular sieves have not been commercially successful.

In the conventional method of carrying out the aforementioned dehydrocyclization, paraffins to be converted are passed over the catalyst, in the presence of hydrogen, at temperatures of the order of 500° C. and pressures of from 5 to 30 bars. Part of the paraffins are converted into aromatic hydrocarbons, and the reaction is accompanied by isomerization and cracking reactions which also convert the paraffins into isoparaffins and lighter hydrocarbons.

The rate of conversion of the hydrocarbons into aromatic hydrocarbons varies with the reaction conditions and the nature of the catalyst.

The catalysts hitherto used have given moderately satisfactory results with heavy paraffins, but less satisfactory results with $C_6$–$C_8$ paraffins, particularly $C_6$ paraffins. Catalysts based on a zeolite of the L family are more selective with regard to the dehydrocyclization reaction; can be used to improve the rate of conversion to aromatic hydrocarbons without requiring higher temperatures, which usually have a considerable adverse effect on the stability of the catalyst; and produce excellent results with $C_6$–$C_8$ paraffins, but stability is a problem.

In one method of dehydrocyclizing aliphatic hydrocarbons, hydrocarbons are contacted in the presence of hydrogen with a catalyst consisting essentially of a type L zeolite having exchangeable cations of which at least 90% are alkali metal ions selected from the group consisting of ions of sodium, lithium, potassium, rubidium and cesium and containing at least one metal selected from the group which consists of metals of Group VIII of the Periodic Table of Elements, tin and germanium, said metal or metals including at least one metal from Group VIII of said Periodic Table having a dehydrogenating effect, so as to convert at least part of the feedstock into aromatic hydrocarbons.

A particularly advantageous embodiment of this method is a platinum/alkali metal/type L zeolite catalyst because of its excellent activity and selectivity for converting hexanes and heptanes to aromatics, but stability remains a problem.

SUMMARY OF THE INVENTION

The present invention overcomes the deficiencies of the prior art by using a catalyst comprising a zeolite of the L family, an alkaline earth metal and a Group VIII metal to reform hydrocarbons. This process gives superior selectivity for converting alkanes to aromatics than shown in prior art processes. The catalyst also gives satisfactory run length. The hydrocarbons are contacted with a catalyst comprising a zeolite of the L family, at least one Group VIII metal (preferably platinum); and an alkaline earth metal selected from the group consisting of barium, strontium and calcium (preferably barium).

Preferably, the zeolite of the L family contains from 0.1% to 5% by weight platinum and 0.1% to 40% by weight barium. The hydrocarbons are contacted with the barium-exchanged type zeolite at a temperature of from 400° C. to 600° C. (preferably 450° C. to 550° C.); an LHSV of from 0.3 to 20; a pressure of from 1 atmosphere to 500 psig (preferably from 50 to 300 psig); and an $H_2$/HC ratio of from 0 to 20:1 (preferably from 1:1 to 10:1).

DESCRIPTION OF THE PREFERRED EMBODIMENTS

In its broadest aspect, the present invention involves a catalyst comprising a zeolite of the L family, an alkaline earth metal and a Group VIII metal and its use in the reforming of hydrocarbons, in particular, the dehydrocyclization of alkanes at a high selectivity.

The term "selectivity" as used in the present invention is defined as the percentage of moles of paraffin converted to aromatics relative to moles converted to aromatics and cracked products, i.e., Selectivity =

$$\frac{100 \times \text{moles of paraffins converted to aromatics}}{\text{moles of paraffins converted to aromatics and cracked products}}$$

Isomerization reactions and alkylcyclopentane formation are counted as no reaction.

The term "selectivity for n-hexane" as used in the present invention is defined as the percentage of moles of n-hexane converted to aromatics relative to moles converted to aromatics and cracked products.

The selectivity for converting paraffins to aromatics is a measure of the efficiency of the process in converting paraffins to the desired and valuable products: aromatics and hydrogen, as opposed to the less desirable products of hydrocracking.

Highly selective catalysts product more hydrogen than less selective catalysts because hydrogen is produced when paraffins are converted to aromatics and hydrogen is consumed when paraffins are converted to cracked products. Increasing the selectivity of the process increases the amount of hydrogen produced (more aromatization) and decreases the amount of hydrogen consumed (less cracking).

Another advantage of using highly selective catalysts is that the hydrogen produced by highly selective catalysts is purer than that produced by less selective catalysts. This higher purity results because more hydrogen is produced, while less low boiling hydrocarbons (cracked products) are produced. The purity of hydrogen produced in reforming is critical if, as is usually the case in an integrated refinery, the hydrogen produced is utilized in processes such as hydrotreating and hydrocracking, which require at least certain minimum partial pressures of hydrogen. If the purity becomes too low, the hydrogen can no longer be used for this purpose and must be used in a less valuable way, for example as fuel gas.

In the method according to the invention, the feed hydrocarbons preferably comprise nonaromatic hydrocarbons containing at least 6 carbon atoms. Preferably, the feedstock is substantially free of sulfur, nitrogen, metals, and other known poisons for reforming catalysts.

The dehydrocyclization is carried out in the presence of hydrogen at a pressure adjusted so as to favor the reaction thermodynamically and limit undesirable hydrocracking reactions by kinetic means. The pressures used preferably vary from 50 to 300 psig, the molar ratio of hydrogen to hydrocarbons preferably being from 1:1 to 10:1.

In the temperature range of from 450° C. to 550° C., the dehydrocyclization reaction occurs with acceptable speed and selectivity.

If the operating temperature is below 450° C., the reaction speed is insufficient and consequently the yield is too low for industrial purposes. Also, the dehydrocyclization equilibria is unfavorable at low temperatures. When the operating temperature is above 550° C., interfering secondary reactions such as hydrocracking and coking occur, and substantially reduce the yield and increase the catalyst deactivation rate. It is not advisable, therefore, to exceed the temperature of 550° C.

The liquid hourly space velocity of the hydrocarbons is preferably between 0.3 and 10.

The catalyst according to the invention is a zeolite of the L family charged with one or more dehydrogenating constituents.

The term "zeolite of the L family" is defined as any zeolite which is made up of cancrinite cages to give a pore structure, the pores of which are bounded by a 12 sided ring wherein the zeolite has dehydrocyclization activity when a Group VIII metal is introduced into the zeolite. Zeolites which are representative of a "zeolite of the L family" include type L zeolite as disclosed in U.S. Pat. No. 3,216,789; AG1 as disclosed in British Pat. No. 1,393,365; AG4 as disclosed in British Pat. No. 1,394,163; AG5 as disclosed in U.S. Pat. No. 4,018,870; AG6; UJ as disclosed in U.S. Pat. No. 3,298,780; and K, Ba-G zeolite. U.S. Pat. Nos. 3,216,789; 3,298,780 and 4,108,870 and British Pat. Nos. 1,393,365 and 1,394,163 are incorporated by reference to show representative zeolites of the L family.

Type L zeolites are synthetic zeolites. A theoretical formula is $M_{9/n} [(AlO_2)_9(SiO_2)_{27}]$ in which M is a cation having the valency n.

The real formula may vary without changing the crystalline structure; for example, the mole ratio of silicon to aluminum (Si/Al) may vary from 1.0 to 3.5.

A more complete description of Type L zeolites is given, e.g., in U.S. Pat. No. 3,216,789 which, more particularly, gives a conventional description of these zeolites with respect to their X-ray diffraction spectrum.

The hydrocarbon sorption pores are channels parallel to the cylinder axis and approximately 7 to 8 Angstroms in diameter.

Zeolites of the L family are conventionally synthesized largely in the potassium form, i.e., in the theoretical formula given previously, most of the M cations are potassium. The M cations are exchangeable, so that a given zeolite of the L family, e.g., a zeolite of the L family in the potassium form, can be used to obtain zeolites of the L family containing other cations, by subjecting the zeolite of the L family to ion exchange treatment in an aqueous solution of appropriate salts. However, it is difficult to exchange all of the original cations, e.g., potassium, since some exchangeable cations in the zeolite are in sites which are difficult for the reagents to reach.

An essential element of the present invention is the presence of an alkaline earth metal in the zeolite of the L family. That alkaline earth metal must be either barium, strontium or calcium, preferably barium. The alkaline earth metal can be incorporated into the zeolite by synthesis, impregnation or ion exchange. Barium is preferred to the other alkaline earths because it results in a somewhat less acidic catalyst. Strong acidity is undesirable in the catalyst because it promotes cracking, resulting in lower selectivity.

In one embodiment, at least part of the alkali metal is exchanged with barium, using techniques known for ion exchange of zeolites. This involves contacting the zeolite with a solution containing excess $Ba^{++}$ ions. The barium should constitute from 0.1% to 40% of the weight of the zeolite.

The catalysts according to the invention are charged with one or more Group VIII metals, e.g., nickel, ruthenium, rhodium, palladium, iridium or platinum.

The preferred Group VIII metals are iridium and particularly platinum, which are more selective with regard to dehydrocyclization and are also more stable under the dehydrocyclization treatment conditions than other Group VIII metals.

The preferred percentage of platinum in the catalyst is between 0.1% and 5%.

Group VIII metals are introduced into the zeolite of the L family by synthesis, impregnation or exchange in an aqueous solution of an appropriate salt. When it is desired to introduce two Group VIII metals into the zeolite, the operation may be carried out simultaneously or sequentially.

By way of example, platinum can be introduced by impregnating the zeolite with an aqueous solution of tetrammineplatinum(II)nitrate, tetrammineplatinum(II) hydroxide, dinitrodiamino-platinum or tetramminepplatinum (II)chloride. In an ion exchange process, platinum can be introduced by using cationic platinum complexes such as tetrammineplatinum(II)nitrate.

An inorganic oxide is used as a carrier to bind the zeolite of the L family containing the Group VIII metal and alkaline earth metal. The carrier can be a natural or a synthetically produced inorganic oxide or combination of inorganic oxides. Typical inorganic oxide supports which can be used include clays, alumina, and silica, in which acidic sites are preferably exchanged by cations which do not impart strong acidity (such as Na, K, Rb, Cs, Ca, Sr, or Ba).

The catalyst can be employed in any of the conventional types of equipment known to the art. It may be employed in the form of pills, pellets, granules, broken fragments, or various special shapes, disposed as a fixed bed within a reaction zone, and the charging stock may be passed therethrough in the liquid, vapor, or mixed phase, and in either upward or downward flow. Alternatively, it may be prepared in a suitable form for use in moving beds, or in fluidized-solid processes, in which the charging stock is passed upward through a turbulent bed of finely divided catalyst.

After the desired metal or metals have been introduced, the catalyst is treated in air at about 260° C. and then reduced in hydrogen at temperatures of from 200° C. to 700° C., preferably 300° C. to 620° C.

At this stage it is ready for use in the dehydrocyclization process. In some cases however, for example when the metal or metals have been introduced by an ion exchange process, it is preferable to eliminate any residual acidity of the zeolite by treating the catalyst with an aqueous solution of a salt of a suitable alkali or alkaline earth element in order to neutralize any hydrogen ions formed during the reduction of metal ions by hydrogen.

In order to obtain optimum selectivity, temperature should be adjusted so that reaction rate is appreciable, but conversion is less than 98%, as excessive temperature and excess reaction can have an adverse affect on selectivity. Pressure should also be adjusted within a proper range. Too high a pressure will place a thermodynamic (equilibrium) limit on the desired reaction, especially for hexane aromatization, and too low a pressure may result in coking and deactivation.

Although the primary benefit of this invention is in improving the selectivity for conversion of paraffins (especially $C_6$-$C_8$ paraffins) to aromatics, it is also surprisingly found that the selectivity for conversion of methylcyclopentane to benzene is excellent. This reaction, which on conventional reforming catalysts based on chlorided alumina involves an acid catalyzed isomerization step, occurs on the catalyst of this invention with selectivity as good as or better than on the chlorided alumina based catalysts of the prior art. Thus, the present invention can also be used to catalyze the conversion of stocks high in 5-membered-ring alkyl naphthenes to aromatics.

Another advantage of this invention is that the catalyst of the present invention is more stable than prior art zeolite catalysts. Stability of the catalyst, or resistance to deactivation, determines its useful run length. Longer run lengths result in less down time and expense in regenerating or replacing the catalyst charge.

EXAMPLES

The invention will be further illustrated by the following examples which set forth a particularly advantageous method and composition embodiments. While the examples are provided to illustrate the present invention, they are not intended to limit it.

EXAMPLE I

An Arabian Light straight run which had been hydrofined to remove sulfur, oxygen and nitrogen was reformed at 100 psig, 2 LHSV, and 6 $H_2$/HC by three different catalysts. The feed contained 80.2 v% paraffins, 16.7 v% naphthenes, and 3.1 v% aromatics, and it contained 21.8 v% $C_5$, 52.9 v% $C_6$, 21.3 v% $C_7$, and 3.2 v% $C_8$.

In the first run, the Arabian Light straight run was reformed at 499° C. using a commercial sulfided platinum-rhenium-alumina catalyst prepared as disclosed in U.S. Pat. No. 3,415,737.

In the second run, the Arabian Light straight run was reformed at 493° C. using a platinum-potassium-zeolite of the L family catalyst formed by: (1) impregnating a potassium-zeolite of the L family with 0.8% platinum using tetrammineplatinum(II)nitrate; (2) drying the catalyst; (3) calcining the catalyst at 260° C.; and (4) reducing the catalyst at 480° C. to 500° C. for 1 hr.

In the third run, the process of the present invention, the Arabian Light straight run was reformed at 493° C. using a platinum-barium-type L zeolite catalyst formed by: (1) ion exchanging a potassium-type L zeolite with a sufficient volume of 0.7 molar barium nitrate solution to contain an excess of barium compared to the ion exchange capacity of the zeolite; (2) drying the resulting barium-exchanged type L zeolite catalyst; (3) calcining the catalyst at 590° C.; (4) impregnating the catalyst with 0.8% platinum using tetrammineplatinum(II)nitrate; (5) drying the catalyst; (6) calcining the catalyst at 260° C.; and (7) reducing the catalyst in hydrogen at 480° C. to 500° C. for 1 hour.

The results of these three runs are shown in Table I.

TABLE I

| | Feed | 499° C. Pt/Re/ Alumina | 493° C. Pt/K/L | 493° C. Pt/Ba/L |
|---|---|---|---|---|
| $C_1$ Wt % Fd | | 2.8 | 5.5 | 3.6 |
| $C_2$ | | 6.6 | 2.5 | 1.3 |
| $C_3$ | | 9.3 | 3.2 | 1.5 |
| $iC_4$ | 0.1 | 5.8 | 0.9 | 0.5 |
| $NC_4$ | 0.5 | 6.8 | 3.8 | 2.4 |
| $iC_5$ | 5.1 | 13.6 | 6.7 | 5.6 |
| $NC_5$ | 11.3 | 9.8 | 12.6 | 12.6 |
| $C_6$+ P + N | 81.3 | 13.4 | 7.8 | 9.3 |
| Benzene | 1.5 | 15.1 | 40.6 | 43.8 |
| $C_7$+ Aromatics | .8 | 15.8 | 12.7 | 15.0 |
| $C_5$+ LV % Yield | | 63 | 69.9 | 74.4 |
| Hydrogen, SCF/B | | 470 | 1660 | 2050 |
| Selectivity, Mole % $C_6$+ P → Aromatics | | 20 | 72 | 87 |

This series of runs shows that the use of a platinum-barium-type L zeolite catalyst in reforming gives a selectivity for converting hexanes to benzene markedly superior to that of the prior art. Notice that associated with this superior selectivity is an increase in hydrogen gas production, which can be used in other processes. Notice also that the hydrogen purity is higher for the Pt/Ba/L run since more hydrogen is produced and less $C_1$ plus $C_2$ are produced.

EXAMPLE II

A second series of runs was made using n-hexane as feed. All runs in this series were made at 490° C., 100 psig, 3 LHSV and 3 $H_2$/HC.

In the first run, a platinum-potassium-type L zeolite was used which had been prepared by the procedures shown in the second process of Example I.

In the second run, a platinum-barium-type L zeolite was used which had been prepared by the procedures shown in the third process of Example I except that the barium nitrate solution was 0.3 molar instead of 0.17 molar. The results of these runs are given below in Table II.

TABLE II

|  | Conversion | | Selectivity for n-hexane | |
| --- | --- | --- | --- | --- |
|  | 5 Hrs. | 20 Hrs. | 5 Hrs. | 20 Hrs. |
| Pt/K/L | 70 | 59 | 76 | 79 |
| Pt/Ba/L | 85 | 85 | 89 | 92 |

Thus, in operation, the incorporation of barium into zeolite of the L family causes a dramatic improvement in selectivity for n-hexane. Notice that the stability of the platinum-barium-type L zeolite is excellent. After 20 hours, there was no drop in conversion when platinum-barium-type L zeolite catalyst was used.

While the present invention has been described with reference to specific embodiments, this application is intended to cover those various changes and substitutions which may be made by those skilled in the art without departing from the spirit and scope of the appended claims.

What is claimed is:

1. A composition comprising:
   (a) a zeolite of the L family;
   (b) at least one Group VIII metal; and
   (c) an alkaline earth metal selected from the group consisting of barium, strontium and calcium.

2. A composition according to claim 1 wherein said alkaline earth metal is barium and wherein said Group VIII metal is platinum.

3. A composition according to claim 2 wherein said zeolite of the L family has from 0.1% to 5% by weight platinum and 0.1% to 40% by weight barium.

4. A composition consisting essentially of:
   (a) a zeolite of the L family;
   (b) an inorganic oxide binder;
   (c) platinum; and
   (d) barium.

5. A composition according to claim 4 wherein said zeolite of the L family has from 0.1% to 5% by weight platinum and 0.1% to 40% by weight barium.

* * * * *